United States Patent [19]
Ziegler

[11] Patent Number: 5,814,010
[45] Date of Patent: Sep. 29, 1998

[54] SAFETY-VAC CAPSULE POLISHER

[75] Inventor: Robert "Zig" Ziegler, Salt Lake City, Utah

[73] Assignee: Allergan, Inc., Irvine, Calif.

[21] Appl. No.: 512,713

[22] Filed: Aug. 8, 1995

[51] Int. Cl.⁶ .................................................. A61B 17/20
[52] U.S. Cl. ............................................................ 604/22
[58] Field of Search ........................... 604/22, 28, 30–34, 604/49, 118, 119, 120, 65, 27, 35, 39; 128/898; 606/107, 169, 161, 162

[56] References Cited

U.S. PATENT DOCUMENTS

| | | | |
|---|---|---|---|
| 0,693,358 | 2/1902 | Westlake | 604/39 |
| 4,825,865 | 5/1989 | Zelman | 606/107 |
| 5,024,654 | 6/1991 | Tyler | 604/35 |
| 5,358,473 | 10/1994 | Mitchell | 604/27 |
| 5,360,397 | 11/1994 | Pinchuk | 604/27 |
| 5,653,724 | 8/1997 | Imonti | 606/169 |

FOREIGN PATENT DOCUMENTS

| | | | |
|---|---|---|---|
| 8909070 | 10/1989 | WIPO | 604/27 |

OTHER PUBLICATIONS

"Sandblasted end cutting tip for posterior capsular vacuuming and polishing" Turtz, AM–Intra–Ocular Implant Soc J. vol. 11, Jan. 1985.

"Safe method for cleaning the Posterior lens Capsule" Isakov et al., J. Cataract Refract Surgery vol. 21, Jul. 1995.

"Ultrasonic Capsule Polisher : A New Instrument and Technique" Levine Ophthalmic Surgery Sep. 1985, vol. 16, No. 9.

"Polishing Methods for the lens capsule: Histology and scanning electron microscopy," Mathey. J. Cataract Refract. Surgery vol. 20, Jan. 1994.

Primary Examiner—Mark Bockelman
Attorney, Agent, or Firm—Walter A. Hackler

[57] ABSTRACT

An irrigation and aspiration handpiece tip for enabling safe vacuuming and polishing of a capsule generally includes an aspiration tube for removal of tissue from an eye which in vacuum communication with a first vacuum port applies vacuum within an eye in order to remove tissue therefrom. The aspiration tube also includes a second vacuum port for controlling vacuum pressure within the vacuum tube, with the first vacuum port and the second vacuum port being disposed in the aspiration tube in a spaced-apart angular relationship with one another. In addition, an irrigation tube is provided for introducing irrigation fluid in order to flush tissue towards the first vacuum port.

13 Claims, 1 Drawing Sheet

SAFETY-VAC CAPSULE POLISHER

The present invention generally relates to ophthalmic surgery and is more particularly directed to irrigation and aspiration of disintegrated lens tissue.

The cataractous lens is one that has become opaque or cloudy and therefore its function of transmitting and focusing light in the eye has been inhibited. In fact, cataracts are the leading cause of blindness in humans.

This condition may be corrected by surgically removing the cataractous lens and replacing it with an artificial intraocular lens. Numerous medically recognized techniques have been utilized for lens removal which utilize, for example, vibrating cutters, which may be ultrasonically driven which cause emulsification or disintegration of the eye lens. Simultaneously with, and/or subsequent to, such lens emulsification, a fluid is inserted for irrigation of the disintegrated lens and a vacuum is provided for the aspiration of the disintegrated lens and the inserted fluids. In order to provide a clean, plaque-free lens capsule, it is, of course, important in this procedure to minimize the amount of capsular opacification.

It should be easily appreciated that a handpiece for irrigation and aspiration of lens tissue requires careful control of both irrigation fluid and vacuum provided thereto. Such control apparatus is described in U.S. Pat. No. 5,268,624 and U.S. Pat. No. 5,342,293, both of these references being incorporated herewith for the purpose of describing control equipment, which may be usable in connection with the present invention.

Fluid flow control, as described in the above-referenced patents for maintaining appropriate vacuum and irrigation fluid, is required to accommodate various vacuum conditions encountered during the evacuation, or aspiration, of tissue. This is because a vacuum port disposed in a handpiece tip by necessity becomes partially or totally occluded during the aspiration of tissue particles from the eye. When this occurs, momentary vacuum level changes occur which may be disruptive to the process of removing the disintegrated tissue.

For example, the passage of a disintegrated tissue particle comparable in size to the opening of a vacuum port causes an immediate rise in vacuum in the conduit providing vacuum to the port. Subsequent passage of the particle through the port is significantly increased, and vacuum is momentarily created. This phenomenon may result in the application of an excess vacuum to surrounding eye tissue which may result in damage thereto.

In view of this effect, elaborate equipment has been designed to specifically control the vacuum in irrigation/aspiration handpiece devices.

The present invention provides for an irrigation/aspiration handpiece tip which controls vacuum level and therefore minimizes risk of capsule rupture by eliminating any residual or excessive vacuum buildup in the handpiece tip or handpiece tubing to prevent unwanted occlusion of the capsule tissue itself. Accordingly, in view of the vacuum control provided by the tip, it may also be used as a simultaneous capsule polisher.

SUMMARY OF THE INVENTION

In accordance with the present invention, an irrigation/aspiration handpiece tip includes an aspiration tube which provides means for removal of tissue from an eye with the aspiration tube including a first vacuum port means for applying vacuum within the eye in order to remove tissue therefrom and pass same into the aspiration tube, the aspiration tube being in vacuum communication with the first vacuum port means.

In addition, the aspiration tube further includes a second vacuum port means for controlling vacuum pressure within the aspiration tube and the first vacuum port means. In this manner, residual or excessive vacuum buildup within the aspiration tube is essentially eliminated.

In addition, an irrigation tube is provided for introducing irrigation fluid to flush tissue towards the first vacuum port means.

More particularly, the first and second vacuum port means may be disposed in the aspiration tube in a spaced-apart angular relationship from one another. The aspiration tube and the irrigation tube may be disposed coaxially with the irrigation tube surrounding the aspiration tube. This feature provides for a compact handpiece tip.

The irrigation tube may include first and second irrigation ports disposed 180° from one another around the irrigation tube in order to provide the dispersal of the irrigation fluid within an eye capsule. In addition, the first and second vacuum port means may be disposed 180° from one another around the irrigation tube in order to provide an angular relationship of approximately 90° between adjacent vacuum port means and irrigation ports.

Further, the first and second vacuum port means may be disposed in a spaced-apart relationship along an axis of the aspiration tube. In order to prevent any direct contact of the second vacuum port means with an endothelium in the eye, a shield may be provided.

More particularly, the shield may comprise a portion of the irrigation tube which surrounds the aspiration tube.

Further, the aspiration tube may include a rounded end, with a first and second port means disposed at a spaced-apart distance from the rounded end.

Importantly, means are provided for polishing an eye capsule which may include a textured surface on a grounded end of the aspiration tube. Therefore, polishing of an eye capsule simultaneously with the irrigation and removal of disintegrated tissue may be performed.

The textured end of the aspiration tube protrudes from the irrigation tube and, in order to facilitate and enhance its polishing capabilities, as well as its application to a capsule surface, the protruding end of the aspiration tube may include a portion disposed at an angle with an access of the irrigation tube.

BRIEF DESCRIPTION OF THE DRAWINGS

The advantages and features of the present invention will be better understood by the following description when considered in conjunction with the accompanying drawings in which.

DETAILED DESCRIPTION

Figure 1:
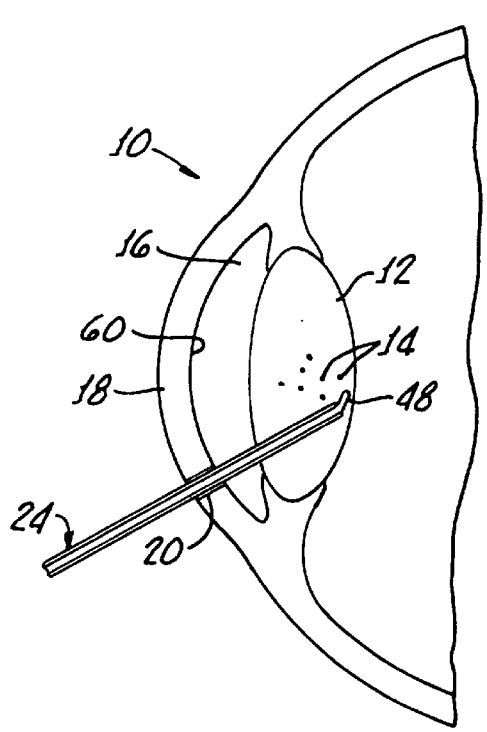
FIG. 1 is a diagrammatic view of the irrigation and aspiration handpiece tip apparatus in accordance with the present invention, as it may be used for both capsule polishing and the irrigation and removal of eye tissue from the capsule.

In FIG. 1, in diagrammatic form, an eye portion 10 is illustrated, showing a posterior chamber, or capsule 12, having tissue particles 14 therein, resulting from prior lens disintegration, all being disposed behind an anterior chamber, or capsule 16, and a cornea 18. An incision 20 in the cornea 18 enables the placement of an irrigation and aspiration handpiece tip 24, in accordance with the present invention, and removal of tissue particles 14 from the posterior chamber 12, while simultaneously polishing a posterior chamber, or capsule, surface 28, as will be hereinafter discussed.

It should be appreciated that the tip 24 is attached to a conventional handpiece (not shown) which in turn is coupled to control apparatus, not shown, for providing irrigation fluid and vacuum to the handpiece tip 24.

Figure 2:
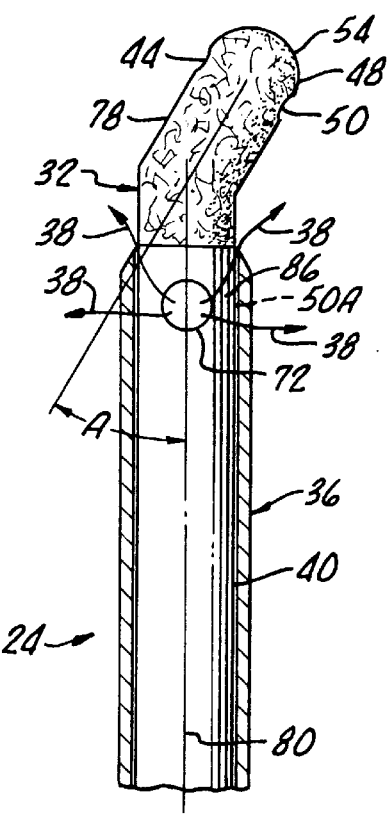
FIG. 2 is an enlarged view of the embodiment of the present invention shown in FIG. 1 which includes a protruding aspiration tube having a textured surface and disposed at an angle to a main body of an aspiration tube, the aspiration tube main body and a surrounding irrigation tube being shown in cross-section below the protruding aspiration tube disposed within an irrigation tube.

FIG. 2 shows an enlarged view of the irrigation and aspiration handpiece tip 24, suitable for both removing disintegrated tissue from a capsule and polishing the capsule surface 28 (see FIG. 1).

Generally included in the handpiece tip 24 is an aspiration tube 32 which provides a means for removal of tissue 14 from the eye 10, coaxially disposed within an irrigation tube 36 which provides means for introducing irrigation fluid, illustrated by arrows 38, through a lumen 40 between the aspiration tube 32 and irrigation tube 36 and out an irrigation port 72. As shown by the arrows 38 the irrigation fluid flows towards a first vacuum port 44 disposed in a tip portion 48 of the aspiration tube 32, the tip portion 48 protruding from the surrounding irrigation tube 36.

The first vacuum port 44 is in vacuum communication with the aspiration tube 36 and applies Vacuum within the eye 10, specifically within the posterior chamber, or capsule 12, in order to remove tissue 14 therefrom and pass same into the aspiration tube 32. Importantly, the aspiration tube 32 includes a second vacuum port 50 which provides means for controlling vacuum pressure within the aspiration tube 32 and the first vacuum port 44. Both the irrigation tube 36 and the aspiration tube 32 may be formed from any suitable material, such as stainless steel or titanium, with the vacuum, or aspiration, ports 44, 50 being between 0.2 mm and 0.3 mm in size and set back, or spaced apart, from a grounded end 54 of the aspiration tube 32.

As also referred to in FIG. 1, the tip 24 design enables the first vacuum port 44 to be disposed and manipulated against a posterior capsule surface 28, with the second vacuum port 50 facing upwardly and at a spaced-apart distance from an endothelium layer of the cornea 18. Thus, the tip 24 may be oriented so that the first vacuum port 44 is directed towards the capsule surface 28, while contact of the second vacuum port 50 with the surface 28 is avoided.

The opposing disposition of the vacuum ports 44 and 50 enable the first vacuum port 44 to be used for aspiration, while the second vacuum port 50 acts as a fluid vent and compensates for excessive vacuum pressure and residual pressure in the system when tissue particles 14 partially or almost totally occlude the first vacuum port 44 during removal therefrom from the capsule 12. The sizing of the two vacuum ports 44, 50 may be utilized to further control the vacuum variation within the aspiration tube 32 and through the port 44. That is, the second vacuum port 50 may be larger or smaller than the first vacuum port 44, in order to establish and provide uniform vacuum pressure during removal of tissue particles 14. Thus, the irrigation and handpiece tip 24 enables and facilitates a method, in accordance with the present invention, of both removing particle tissue 14 from the eye 10, with simultaneous polishing of the capsule, or chamber, surface 28.

As shown in FIG. 2, the first and second vacuum ports 44, 50 may be directly opposing, that is, disposed 180° from one another around the irrigation tube 32.

Importantly, the aspiration tube tip 48 is textured (for example, by sandblasting) for the last 3 mm thereof, or for the entire portion (as shown) protruding from the irrigation tube, or sleeve, 36. This texturing provides a means for polishing the eye capsule surface 28 by urging the textured aspiration tube tip 48 against the surface 28 and manually maneuvering the textured aspiration tube tip 48 while simultaneously vacuuming, or removing, tissue particles 14 from the capsule 12.

Figure 3:
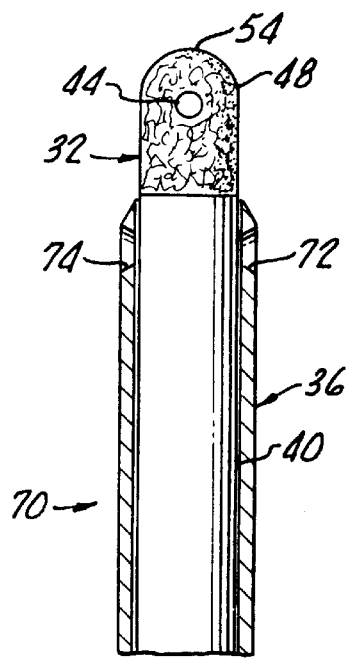
FIG. 3 is a cross-sectional view of another embodiment of the present invention in which the protruding portion of the aspiration tube is coaxial with the main body of the aspiration tube and the irrigation tube, the aspiration tube main body and a surrounding irrigation tube being shown in cross-section below the protruding portion of the aspiration tube.
Figure 4:
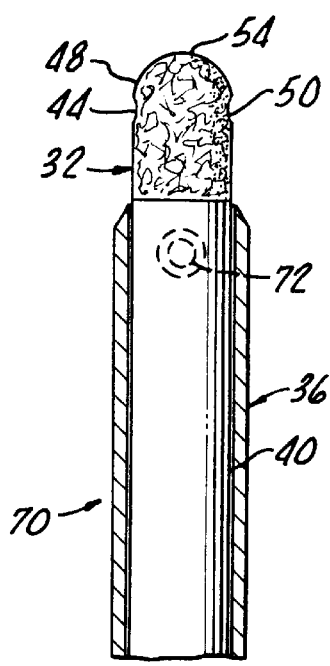
FIG. 4 is a side view of the embodiment shown in FIG. 3.
Figure 5:
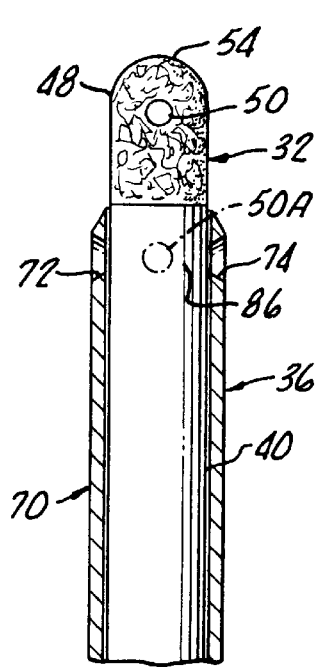
FIG. 5 is a back view of another embodiment of the present invention in which a second vacuum port is disposed beneath a portion of an irrigation tube in order to provide a shielded vacuum port.

As shown in FIG. 2 and in the alternative embodiment 70 shown in FIGS. 3, 4 and 5, the irrigation tube 36 may include first and second irrigation ports 72, 74, disposed at approximately 180° from one another, which provide for the dispersement of irrigation fluid. In addition, the vacuum ports 44, 50 are disposed at an angular relationship at approximately 90° from adjacent irrigation ports.

As shown in FIG. 2, the embodiment 24 includes a portion 78, which may be approximately 1.75 mm in length, disposed at an angle A, of about 30° from an access 80 of the aspiration tube 32 and irrigation tube 36.

In order to assure that the second vacuum port 50 does not contact any other eye surfaces, it may be alternatively placed as indicated by the dashed lines 50A in FIGS. 2 and 5 beneath a portion 86 which accordingly provides a shield for the alternately disposed vacuum port 50A.

Briefly referring to FIGS. 3, 4 and 5, the alternative embodiment 70 of the present invention includes an aspiration tube 32 which does not include an angled portion; otherwise, all character references shown throughout the figures of the present application refer to identical items. The embodiment 70 may be a preferred handpiece tip for some procedures.

Although there has been hereinabove described specific embodiments of the present invention for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

Is claimed is:

1. An irrigation and aspiration handpiece tip comprising:
   aspiration tube means for removal of tissue from an eye, said aspiration tube means including first vacuum port means, in vacuum communication with said aspiration tube means, for applying vacuum within the eye in order to remove tissue therefrom and pass same into said aspiration tube means, said aspiration tube means further including second vacuum port means for controlling vacuum pressure within said aspiration tube means and said first vacuum port means, said first and second vacuum port means being disposed in said aspiration tube means in a spaced-apart angular relationship from one another, said second vacuum port means being of different size than said first vacuum port means in order to control vacuum pressure within said aspiration tube means;

irrigation tube means for providing irrigation fluid to flush tissue toward said first vacuum port means; and means, disposed on said aspiration tube means for polishing an eye capsule.

2. The handpiece tip according to claim 1 wherein said aspiration tube means and irrigation tube means are disposed coaxially with said irrigation tube means surrounding said aspiration tube means.

3. The handpiece tip according to claim 2 wherein said irrigation tube means comprises first and second irrigation ports disposed 180° from one another around said irrigation tube means.

4. The handpiece tip according to claim 3 wherein said first and second vacuum port means are disposed 180° from one another around said aspiration tube means and the second vacuum port means is larger than the first vacuum port means.

5. The handpiece tip according to claim 4 wherein the vacuum port means and irrigation ports are disposed at an angular relationship of approximately 90 degrees from one another.

6. The handpiece tip according to claim 4 wherein said first and second vacuum port means are disposed in a spaced-apart relationship along an axis of said aspiration tube means.

7. The handpiece tip according to claim 2 further comprising shield means for preventing direct contact of said second vacuum port means with an endothelium of said eye.

8. The handpiece tip according to claim 7 wherein said shield means comprises a portion of said irrigation tube means.

9. The handpiece tip according to claim 1 wherein said aspiration tube means includes a rounded end and the first and second vacuum port means are disposed at a spaced distance from said rounded end.

10. The handpiece tip according to claim 1 wherein said means for polishing an eye capsule includes a textured surface on an end of said aspiration tube means.

11. The handpiece tip according to claim 10 wherein the aspiration tube means end is rounded.

12. The handpiece tip according to claim 11 wherein said aspiration tube means and irrigation tube means are disposed coaxially with the end of said aspiration tube means protruding from said irrigation tube means.

13. The handpiece tip according to claim 12 wherein the protruding end of said aspiration tube means includes a portion disposed at an angle with an axis of said irrigation tube means and said second vacuum Port is disposed on an underside of the protruding end in order to prevent inadvertent contact thereof with tissue.

* * * * *